United States Patent [19]
Schneidt

[11] Patent Number: 5,702,421
[45] Date of Patent: Dec. 30, 1997

[54] CLOSURE DEVICE FOR CLOSING A VASCULAR OPENING, SUCH AS PATENT DUCTUS ARTERIOSUS

[76] Inventor: Bernhard Schneidt, Johanniter Strasse 14, 63571 Gelnhausen, Germany

[21] Appl. No.: 585,114

[22] Filed: Jan. 11, 1996

[30] Foreign Application Priority Data

Jan. 11, 1995 [DE] Germany ............... 295 00 381.2 U
Aug. 24, 1995 [EP] European Pat. Off. ......... 95113341.2

[51] Int. Cl.$^6$ ........................................... A61B 17/08
[52] U.S. Cl. .......................... 606/213; 600/32; 604/285; 606/215
[58] Field of Search ................. 606/213, 215, 606/151; 600/32; 623/11; 604/285, 286

[56] References Cited

U.S. PATENT DOCUMENTS

| | | |
|---|---|---|
| 3,874,338 | 4/1975 | King et al. . |
| 4,007,743 | 2/1977 | Blake . |
| 5,108,420 | 4/1992 | Marks . |
| 5,334,137 | 8/1994 | Freeman . |
| 5,334,217 | 8/1994 | Das .................................. 606/213 |
| 5,382,260 | 1/1995 | Dormandy, Jr. et al. . |
| 5,397,331 | 3/1995 | Himpens et al. ................. 606/151 |

FOREIGN PATENT DOCUMENTS

| | | |
|---|---|---|
| 362113 | 4/1990 | European Pat. Off. . |
| 541063 | 5/1993 | European Pat. Off. . |
| 233303 | 2/1986 | German Dem. Rep. . |
| 4222291 | 1/1994 | Germany . |
| 5724132 | 1/1979 | Japan . |
| 9316650 | 9/1993 | WIPO . |
| 9409705 | 5/1994 | WIPO . |

*Primary Examiner*—Michael Buiz
*Assistant Examiner*—Tina T. D. Pham
*Attorney, Agent, or Firm*—Dennison, Meserole, Pollack & Scheiner

[57] ABSTRACT

The invention relates to a closure device (10) for closing an anatomical anomaly in the form of a vascular opening (80), such as patent ductus arteriosus, atrial septal defect, foramen ovale or ventricular septal defect, including a closure body (14) that extends at least within the vascular opening and wirelike, elastic locking members (30, 32, 34). In order to improve a fixation of the closure device and to preclude injuries, it is proposed that the locking members (30, 32, 34), on their free ends, be embodied spherically or in lentiform fashion or be provided with spherical or lentiform elements (40).

12 Claims, 6 Drawing Sheets

CLOSURE DEVICE FOR CLOSING A VASCULAR OPENING, SUCH AS PATENT DUCTUS ARTERIOSUS

BACKGROUND

The invention relates to a closure device for closing an anatomical anomaly in the form of a vascular opening, such as patent ductus arteriosus (PDA), atrial septal defect, foramen ovale or ventricular septal defect, including a closure body that extends at least within the vascular opening and wirelike, elastic locking means extending outside the vascular opening, which are embodied as spherical or lentiform on their free ends or are provided with spherical or lentiform elements and are preferably polished laser welded beads or polished titanium balls. The invention also relates to a closure device for closing an anatomical anomaly in the form of a vascular opening, such as patent ductus arteriosus, atrial septal defect, foramen ovale or ventricular septal defect, including a closure body with an axially extending middle part.

The human blood circulation comprises a coronary circuit and a pulmonary circuit. In the embryonic phase of human development, the two circuits are joined to one another by the ductus arteriosus. The ductus connects the aorta (circulation to the body) to the pulmonary artery (pulmonary circuit). In normal development of an infant, this ductus grows shut after birth. If development is defective, it can happen that the ductus does not grow shut, and as a result the two blood circuits are still joined even after birth. This can severely shorten the infant's life expectancy.

It is known to close the PDA by surgical intervention. However, this intervention is extremely expensive and involves risk to the patient.

It is also known for the patent ductus arteriosus to be closed by means of an IVALON® foam plug (Porstmann's technique). A guide splint is fed through a femoral artery into the aortal through the ductus into the pulmonary artery, and from there through the right ventricle and the right atrium of the heart and finally through the opposite femoral veins back to the outside. Next, the ductus plug is thrust into the ductus, where it is "wedged firm". Because of the great difference in pressure between the aorta and the pulmonary artery, stringent demands are made of the locking of the ductus plug inside the ductus.

Relatively large plugs must therefore be used, which are compressed in length by a factor of 10 and are 30% larger than the diameter of the ductus. Correspondingly large gateways are needed to thread the plug into the femoral artery. In infants, the lumen of the vessel is too small, and in children weighing less than 30 kg it is often too small for such an intervention to be made.

The closure device of the type referred to at the outset can be found in East German Patent Disclosure DD 233 303 A1. In the known closure device, the closure body has a single-shell hyperboloid-like outline and may comprise metal, a metal alloy, plastic and similar materials. Extending outside the closure body are wirelike locking means that terminate in a point, so the danger exists that vessel walls will be injured.

For implanting the closure device, the closure device is grasped by a holding wire extending inside a securing tube and is thrust through a catheter. Because of the shape of the closure body and the fact that the ends of the locking means terminate in a point, there is not only considerable danger of injury to a patient but also the possibility of retracting a mispositioned closure device back into the catheter.

SUMMARY OF THE INVENTION

The object of the present invention is to improve a closure device of the type referred to at the outset in such a way that locking of the closure device inside the vascular opening is improved, thus making a secure closure available. In addition, the implantation should be facilitated, with the possibility of correcting misplacements without difficulties.

According to the invention, this object is substantially attained in that the locking means are positionally fixed with the closure body on the face end by suturing or extend entirely or nearly entirely within the closure body. By the embodiment according to the invention of the closure device, it is assured that injury to the vessel walls by the locking means is precluded. As a result, there is the advantage that upon implantation of the closure device, a change in position of the closure is easily possible. The spherical or lentiform ends of the locking means also assure that when there is a major pressure difference in the vessels joined by the ductus, the fixing elements that normally contact the inner walls of the vessels cannot cause injury from motion of the closure device. The spherical ends also prevent injury even if the device might be transported through the vessels without being secured by the catheter. The locking elements, which can also be called fixing elements, preferably extend in raylike fashion from the closure body. Alternatively, it is possible to embody the locking means as loops, which present larger contact surfaces for the locking means along the inner walls of the vessel. The locking elements, which perform the function of spring elements, may comprise platinum, titanium, or other suitable materials. It is also possible to use a titanium-nickel alloy with a platinum or titanium coating. The spherical or lentiform, i.e., oval, ends may be polished titanium balls or laser welded beads.

The locking means themselves are positionally fixed with the closure body on the face end by suturing. Alternatively, the locking means can extend entirely or nearly entirely within the closure body and be foamed into it. This provision assures that the closure body, if it is a plastic part, cannot be displaced or compressed as a result of the pressure difference at the ends of the vascular opening.

The locking means may be joined together via a middle part extending axially inside the closure body. By means of the middle part, a connection can then be made with the locking means associated with the various vessels. The middle part itself may be embodied in one piece or in multiple parts, for instance in telescoping fashion. Receptacles for the locking means can be embodied as holes made in the end portions of the middle parts. The end portions of the middle part may be embodied as separate receptacles which are joined, for instance by welding, to the middle part.

According to the invention, each PDA should be closed as tightly as possible and with as much implant composition as possible. This also assures that the space in the guide catheter will always be optimally filled; that is, the implant material (IVALON®) or similar suitable material can be displaced to the applicator tongs with only a single expenditure of force. To preclude loosening or uncontrolled shifting of the implant relative to the locking elements, it is provided according to the invention that these elements are always sutured to the implant. To achieve optimal filling of the ductus, the device may be embodied either with a middle part or without a middle part.

In a further feature of the invention, a locking means, beginning at this middle region, and/or the middle part of the axial length of the closure body may have a formed-on feature such as a coupling, which can be grasped by guide tongs. This preferably spherical formed-on feature affords the possibility of easy manipulation of the closure device inside a guide catheter by means of flexible guide tongs.

After implantation of the closure device, in order to not release it from the guide tongs until proper positioning has been accomplished, or optionally to enable retraction of the closure device into the catheter, a feature of the invention that should be especially emphasized provides that there is a safety connection, such as a safety thread, between the closure device and the guide tongs.

To assure especially good sealing off of the vascular opening (shunt connection), it is also provided that the closure body, which can also be called an implant, is embodied as rotationally symmetrical and at least in some portions as frustoconical. The implant is used in such a way that a tapered side of the implant points in the direction of the vessel having the lesser pressure. The surface with the enlarged cross section points in the direction of the vessel having the higher pressure. As a result, the shunt connection is sealed off in wedgelike fashion. Slipping of the implant inside the shunt connection can also be averted.

In a further feature of the invention, the implant may have a cylindrical base region and a frustoconical tip region; the frustoconical tip region has a surface that follows either a frustoconical jacket or a concave form.

To attained a preferred wedge shape, the base region has a base surface with a diameter D1 that is at least 4 mm larger than a mean diameter MD of the implant. The mean diameter MD is measured in the middle of the axial length of the implant at the frustoconical tip region.

In an independent claim it is proposed that protruding metal wires or bristles that form a brushlike body begin at the middle part of the closure body. When a correspondingly embodied closure body is inserted, it is true that a vascular opening is not closed directly. However, as a result of the protruding bristles or wires the wall of the opening is injured, which promotes clot formation, and closure of the opening thus ensues. Plastic fiber threads can also begin at the middle part and also promote clot formation.

If wires or bristles beginning at the middle part extend outside the vascular opening, then they should be embodied as lentiform or spherical on their ends, in the manner described above, so as to preclude injury to the vessel walls in this region.

Further details, advantages and characteristics of the invention will become apparent not only from the claims and from the characteristics to be found in them—independently and/or in combination—but also from the ensuing description of preferred exemplary embodiments to be found in the drawing. Shown are:

BRIEF DESCRIPTION OF THE DRAWINGS

FIG. 7b is a plan view, in the axial direction of the claw elements of the insertion tongs of FIG. 7a;

DETAILED DESCRIPTION OF THE PREFERRED EMBODIMENT

Figure 1:
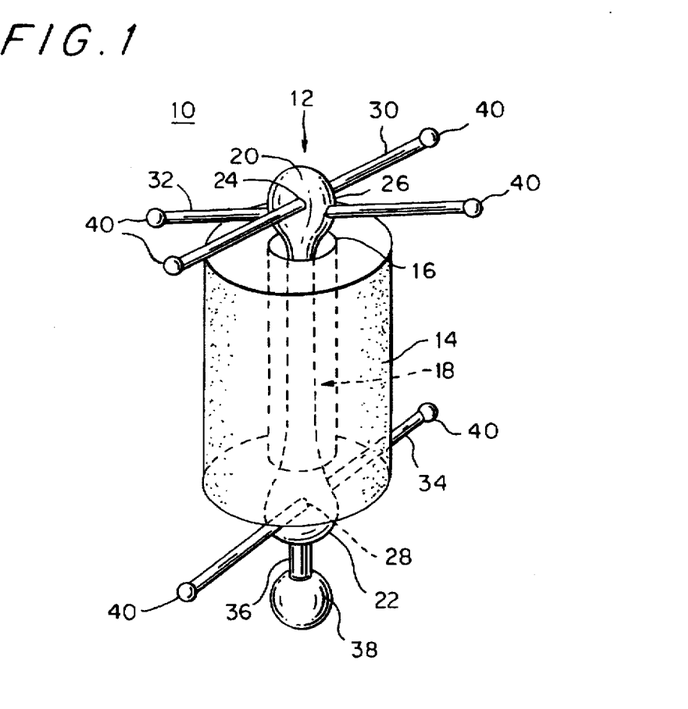
FIG. 1, a first embodiment of a closure device in a perspective view.

FIG. 1 shows a first embodiment of a closure device (10), which—without any restriction to the invention—will be called a ductus stopper. The ductus stopper (10) including a locking device (12) and a preferably cylindrical implant (14) as its closure body. The implant (14) may comprise a foamlike material such as IVALON®, which is distinguished by the fact that it is well tolerated by the human body and forms a bond with the vascular tissue surrounding it. Axially, the closure body (14) that closes a vascular opening has a hole (16), which is embodied for receiving the locking device (12). Naturally, the closure body (14) can also axially surround the locking device (12).

The locking device (12) has a middle part (18), which in a first embodiment is embodied in one piece. The middle part (18) has end regions (20), (22), in which holes (24), (26), (28) are made, which serve to receive locking means—also called fixing elements (30), (32), (34). The middle part (18), on one end region (22), also has a spherical or cylindrical coupling element (38), preferably spaced apart from it by a strut (36) or constriction. The middle part (18), the strut (36) and the spherical coupling (38) have a common center axis.

The middle part (18) is preferably ground or turned from a single piece, using a round material, for instance of titanium or some other material such as a platinum alloy, having a diameter of approximately 1 mm. This material is ground or turned to a diameter of approximately 0.4 mm to 0.6 mm between the end regions (20), (22), primarily in order to gain more space in the catheter for the IVALON®, for example. The flexibility is assured by the play at the coupling of the mouth of the tongs. The axially central hole in the mouth of the tongs is slightly larger than the diameter of the middle part in the region where it is grasped. The end regions (20), (22) may have a spherical or cylindrical form. The holes (24, 26) made in the end regions (20) extend one above the other and are preferably offset from one another by an angle of 90°.

The fixing elements (30), (32), (34) may comprise highly elastic titanium wire, and on their ends they have polished laser welded pearls (40), in order to prevent injuries to the vessel walls. The ends may also be provided with polished titanium balls, which are welded to the ends of the wirelike fixing elements (30, 32, 34).

Figure 2:
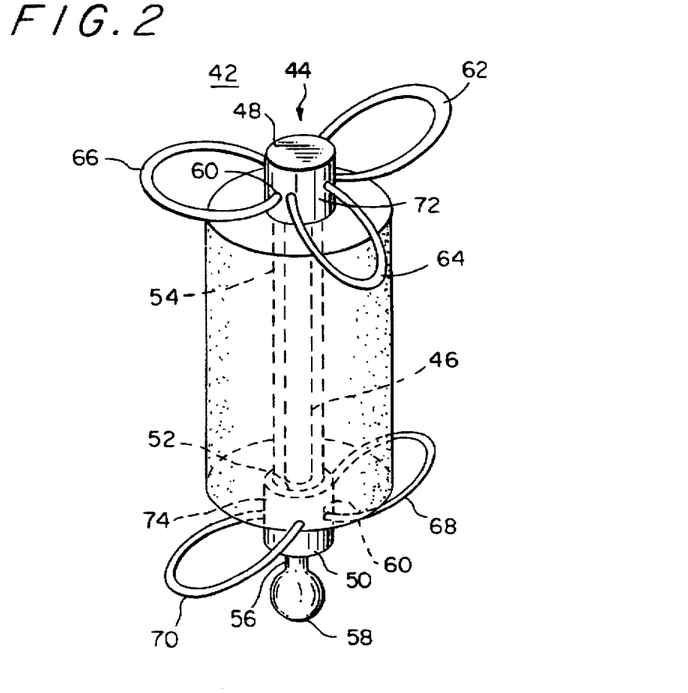
FIG. 2, a second embodiment of the closure device in a perspective view.

FIG. 2 shows a second embodiment of a ductus stopper (42), which is substantially distinguished from the embodiment of FIG. 1 in having an altered embodiment of a locking device (44). The locking device (44) has a middle part (46), to the ends of which mounts (48), (50) are secured, for instance by welding. The mounts (48), (50) have a cylindrical shape and have receptacles (52), (54) for the middle part (46). A strut (56) is formed onto the side of the mount (50) opposite the receptacle (52) and merges with a spherical coupling (58). As in FIG. 1, the middle part (46), the strut (56), and the spherical coupling (58) of FIG. 2 are located on a common center axis.

The mounts (48), (50) have receptacles (60) for receiving locking means or fixing or retaining elements (62), (64), (66), (68), (70). The receptacles (60) are made, resting on a circumferential line, in outer surfaces (72), (74) of the mounts (48), (50). To form a loop, the fixing or retaining elements (62), (64), (66), (68), (70) are each fastened in their ends in the receptacles (60) of the retaining elements (48), (50). The retaining or fixing elements (62), (64), (66), (68), (70), which are preferably of highly elastic titanium wire, are mechanically fixed in the receptacles (60). The preferred looplike embodiment of the fixing or retaining elements (62), (64), (66), (68), (70) prevents damage to vessel walls. It also achieves the largest possible area of contact on the inner walls of the vessels.

Figure 3:
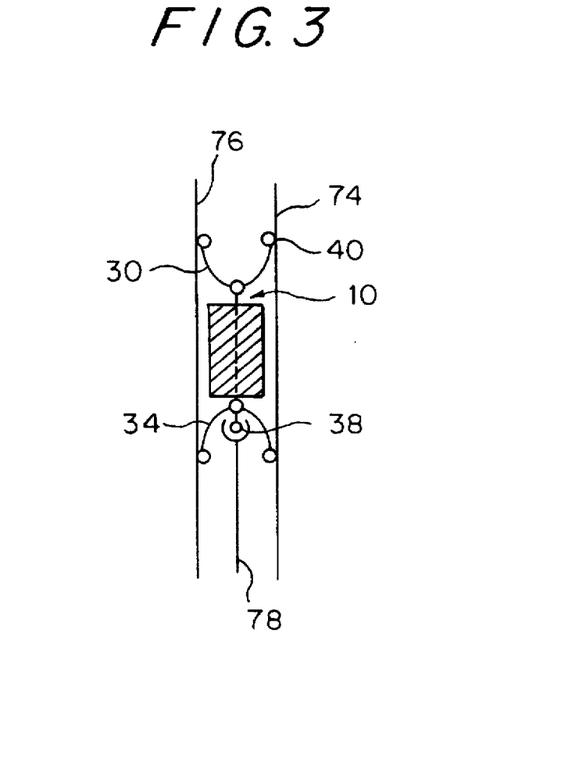
FIG. 3, the closure device of FIG. 1, inserted into a guide catheter.

FIG. 3 shows the ductus stopper (10) of FIG. 1, placed in a guide catheter (74). The ductus stopper (10) rests with its curved fixing elements (30), (32), (34) and the polished laser-welded beads or titanium balls (40) on an inner wall (76) of the catheter (74). Because of the pointwise contact of the ductus stopper (10) inside the catheter (74), ease of motion of the ductus stopper (10) becomes possible. In the original state, the cylindrical sealing implant, such as IVALON®, can be inserted into the catheter (74) easily together with the locking device (12), (44). Inside the catheter, the ductus stopper (10) is retained by flexible guide tongs (78), which engage the spherical or cylindrical coupling (38) of the ductus stopper (10).

Figure 4:
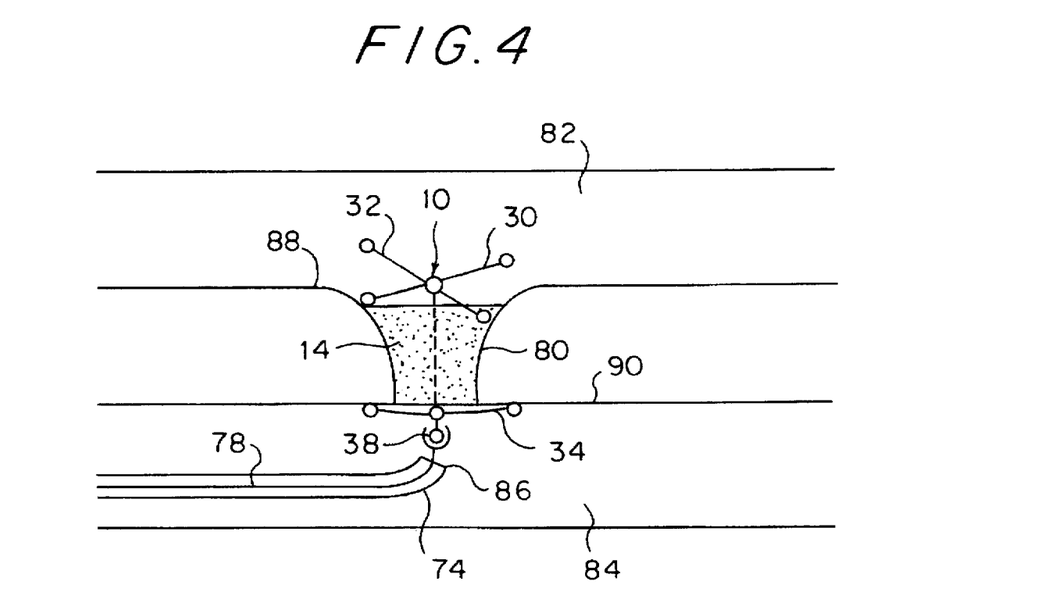
FIG. 4, the closure device of FIG. 1 inserted to its place of use.

FIG. 4 shows the ductus stopper (10) inserted into a ductus (80). The ductus stopper (10) is introduced into the ductus (80) via the catheter (74), for example from a leg vein via the inferior vena cava, right atrium, right ventricle and pulmonary artery (84). The catheter (74) or the guide tongs (78) have diameters that are in the range from 2 mm to 6 mm. Particularly in the case of small diameters, such as 2.5 mm, the possibility exists of treating even infants and small children. The ductus (80) here forms the communication between a vessel (82), such as the aorta, and another vessel (84), such as the pulmonary artery. In the arrangement shown in FIG. 3, the ductus stopper (10) is inserted into the ductus (80) by means of the catheter (74). To that end, the catheter (74), with the ductus stopper (10) in place in it, is passed through the pulmonary artery (84) into the ductus (80), until an upper edge (86) of the catheter (74) protrudes into the aorta (82). The ductus stopper (10) is located at the level of the ductus (80). Next, the wall (76) of the catheter (74) is moved, with the position of the ductus stopper (10) being kept constant, in the direction of the artery (84), and as a result the fixing elements (30, 32) can press against an inner wall (88) of the aorta (82). Next, the implant (14) is exposed, so that it conforms to the inner wall (90) of the ductus (80). The position of the ductus stopper (10) is kept constant by the guide tongs (78), which engage the coupling (38) of the ductus stopper (10). Once the implant (14) is exposed, the fixing element (34) toward the pulmonary artery (84) is finally exposed and can thus conform to the inner wall (92) of the pulmonary artery (84).

From the contact with liquid, such as blood, the implant (14) swells up, so that the ductus (80) is tightly closed. By means of the fixing elements (30), (32), (34) contacting the inner walls (88), (90), an axial displacement of the implant (14) caused by the high pressure difference between the vessels (82), (84) is prevented. For further fixation of the implant, it is provided that the implant (14) is sutured to the locking device (12) by suturing material. This prevents relative motion between the implant (14) and the locking device (12). Once the ductus stopper has been inserted inside the ductus (80), and the fixing elements (30, 32, 34) rest on the inner walls (88), (90), of the vessels (82), (84), the flexible guide tongs (78) can be released from the spherical coupling (38) and removed from the pulmonary artery (84). The geometry of the implant (14) is designed such that the end regions (20), (22) and the fixing elements (30), (32), (34) are at least partly encased by the swollen implant material. By means of the device of the invention, a secure duct closure can thus be realized in a simple, economical way.

Figure 5:
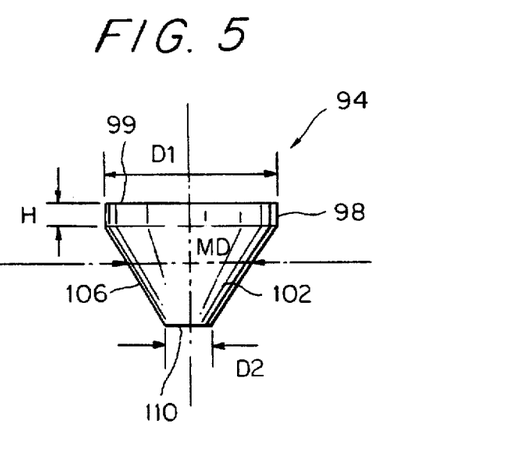
FIG. 5, a first embodiment of a closure body for a closure device, seen in section.
Figure 6:
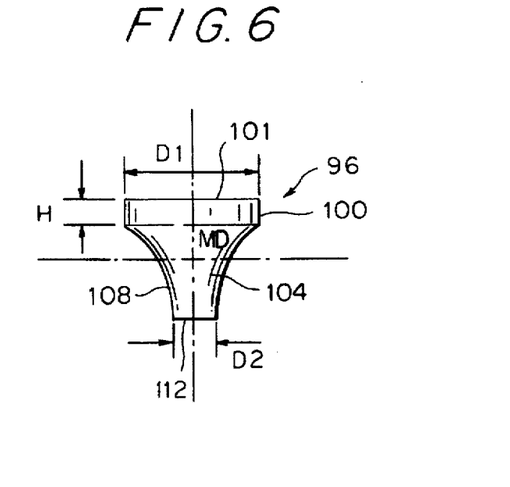
FIG. 6, a second embodiment of a closure body, in a sectional view.

FIGS. 5 and 6 show different embodiments of implants (94), (96). The implants (94), (96) are rotationally symmetrical bodies which at least in some regions are embodied frustoconically and preferably comprise a foam, such as Ivalon®.

The implants (94), (96) substantially comprise a cylindrical base region (98), (100), which is adjoined by a frustoconical tip region (102), (104). The cylindrical base region (98), (100) has a diameter (D1) in the range of 12 to 14 mm, for example, which however is at least 4 mm larger than a mean diameter MD of the implant (94, 96). A diameter of the frustoconical tip region (102, 104) that is ascertained in the middle between the base surface (99), (101) and the end face (110), (112) is defined as the mean diameter MD. The end face (110), (112) has a diameter (D2), which is preferably in the range between 4 and 6 mm. The cylindrical base region (98), (100) also has a height (H), which is preferably 2 mm.

As shown in FIG. 5, the cylindrical base region 98 is adjoined by a frustoconical tip region (102), whose surface (106) follows the form of a truncated cone.

Alternatively, the frustoconical tip region (104) may, as shown in FIG. 6, have a surface (108) that extends in concave fashion.

Figure 7A:
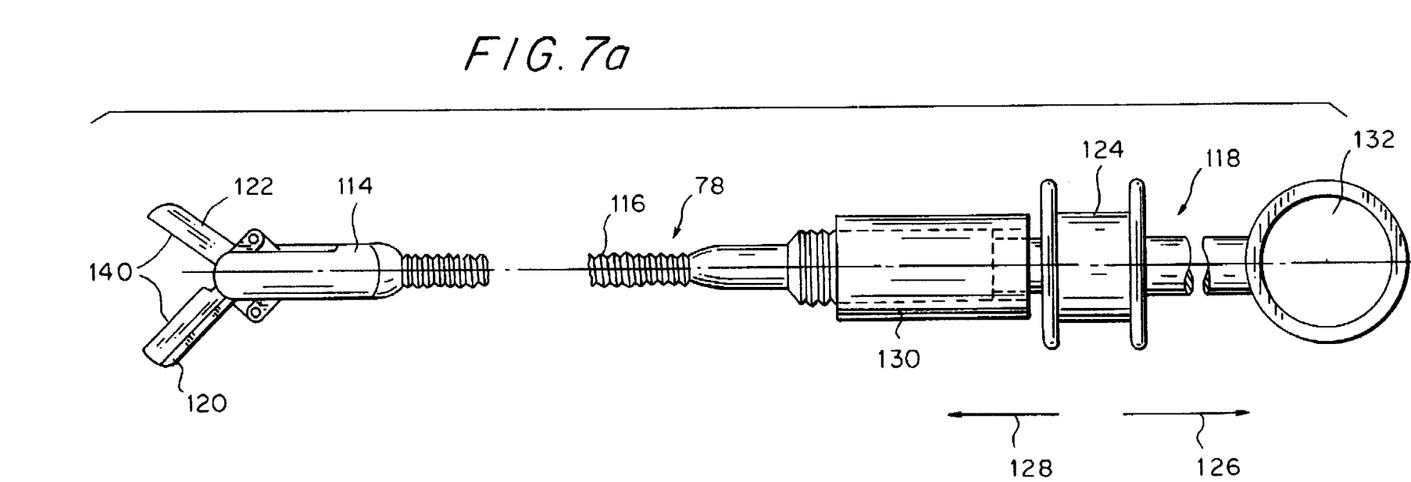
FIG. 7A, insertion tongs for inserting a closure device through a catheter.

In FIG. 7a, the flexible insertion tongs (78) for the ductus stopper (10), (42) are shown. The insertion tongs (78) have a tong body (114), which is joined to a handle (118) via a flexible intermediate part (116). The tong body (114) comprises two shell-like claw elements (120, 122), which communicate with an actuating ring (124) of the handle (118) via a rod linkage (not shown) that extends inside the flexible intermediate part (116). By displacement of the actuating ring (124) in the direction of the arrow (126), the shell-like claw elements (120), (122) can be closed. A motion of the actuating ring (124) in the direction of the arrow (128), conversely, causes the claw elements (120), (122) to open.

In the closed position of the claw elements (120), (122), the actuating ring (124) can be locked by a threaded sleeve (130) or compression spring. For opening the claws (120), (122), it is accordingly necessary to loosen the threaded sleeve (130), to allow the actuating ring (124) to be displaced in the direction of the arrow (128). The guide tongs (78) themselves can be held by way of a holder ring (132).

Figure 7B:
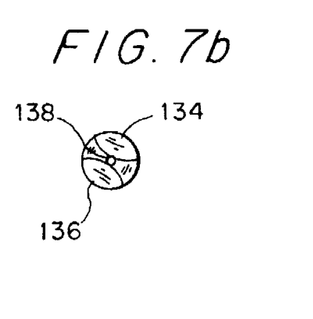

FIG. 7b is a plan view in the axial direction on the claw elements (120, 122) when they are in the closed position. The claw elements (120, 122) each have respective recesses (134), (136), which in the closed position of the claws form a preferably circular opening (138) in the axial direction of the insertion tongs (78). The opening (138) serves to receive the strut (36), (56) formed onto the locking means (12), (44), onto which strut the formed-on feature (38), (58), such as a coupling, is formed in the axial length. In the closed position of the claws (120, 122), the formed-on feature (38), (58) is located in a hollow space (140) formed by the tub-shaped claws.

Figure 7C:
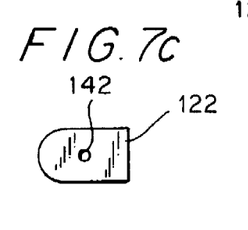
FIG. 7c is a side view of the claw elements of FIG. 7b.

FIG. 7c shows a side view of the claw element (122). The claw wall has a hole (142) for receiving a safety thread (144) that serves to lock the ductus stopper (10), (42).

Figure 8:
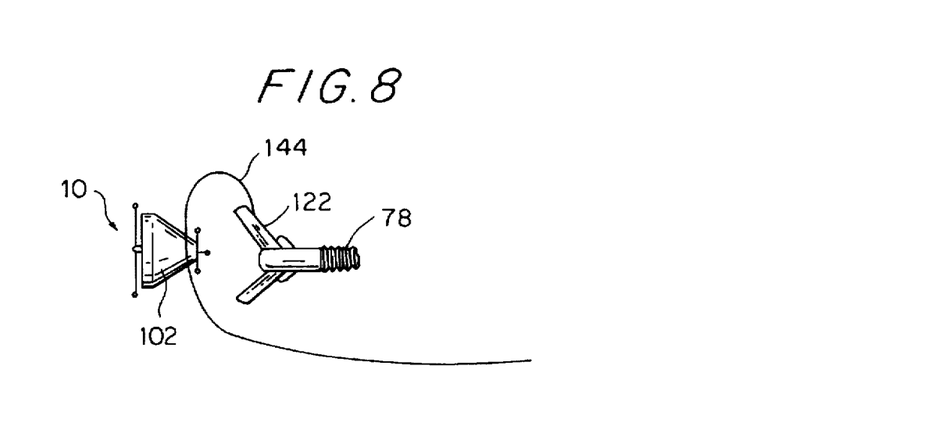
FIG. 8, a closure device connected to the insertion tongs via a safety thread.

FIG. 8 shows the securing of the closure device (10) to the insertion tongs (78) by means of the safety thread (144). To that end, the safety thread (144) is passed through the implant (102) and knotted at one end, not shown, in the opening (142) see FIG. 7c, of the claw element (122). As a result of the safety thread (144), the closure device (10) is secured even if the claw elements (120), (122) open unintentionally, or if the ductus stopper should slip after an intentional decoupling. This lessens the danger of an embolism. Once the implantation has been successfully accomplished, the safety thread (144) is pulled back through the guide catheter along with the insertion tongs (78), which presents no problems at all.

Figure 9:
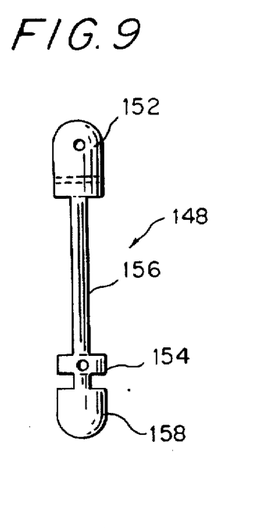
FIG. 9, a detail view of a middle part of a closure device.
Figure 10:
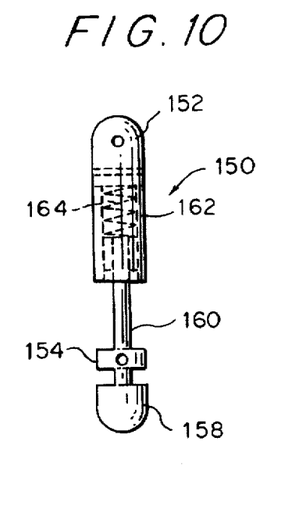
FIG. 10, a further embodiment of a middle part of a closure device.

In FIGS. 9 and 10, special embodiments of middle parts (148) and (150) are shown, which extend in the axial direction of a closure body and have reinforcements (152), (154) on the ends; these reinforcements are penetrated by locking or fixing means, not shown, and are connected to them mechanically. In addition, the locking means should be sutured to the closure body with a triple or double seam with three knots, in order to prevent relative motion of the closure body along the middle part (148) and (150).

The middle part (148) extends with a strutlike middle portion (156) inside a closure body, not shown. The end regions (152) and (154) of enlarged cross section extend outside the closure body, at least in the non-implanted state of the closure device.

On the end, specifically in the region of the reinforced end (154), each middle part (148), (150) has formed-on features (158), described in conjunction with FIGS. 1, 2, 3 and 4 and acting as a coupling, so that the middle part (148), (150) and hence the particular closure device can be grasped by insertion tongs.

If the middle part (148) is embodied in one piece as shown in FIG. 9, then the embodiment of FIG. 10 is adjustable in length, because a strutlike lower portion (160) is adjustable in telescoping fashion relative to the upper portion (162) that surrounds it. A connection via a tension spring (164) preferably exists between the outer portion (162) and the strutlike inner portion (160), resulting in an optimal conformation to the length of a ductus to be closed.

Figure 11:
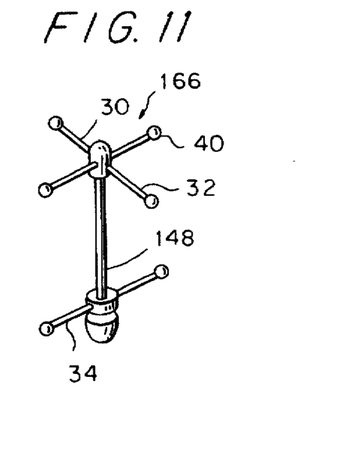
FIG. 11, a skeleton of a closure device.
Figure 12:
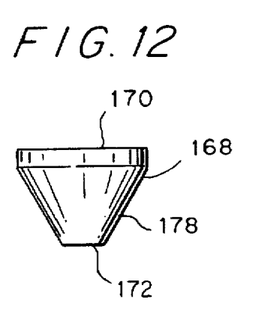
FIG. 12, a preferred embodiment of a closure body.
Figure 13:
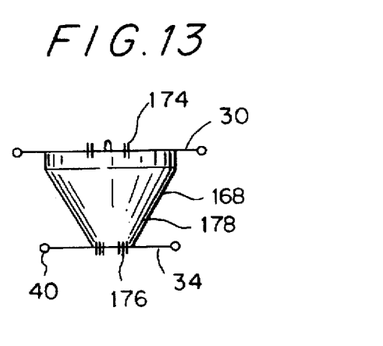
FIG. 13, the closure body of FIG. 12 with locking means connected to it.
Figure 14:
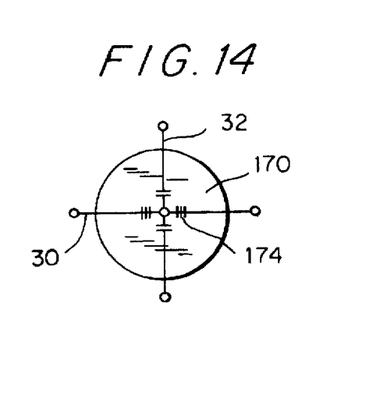
FIG. 14, the closure body of FIG. 13 in a plan view.

In FIG. 11, a locking device (166), which can also be called a skeleton, for a closure device is shown; it comprises a middle part (148), corresponding to the example of FIG. 9, and on its ends locking or fixing elements (30, 32, 34) that begin at the middle part and have polished titanium balls (40) on their ends.

A corresponding skeleton (166) is now surrounded by a closure body (168), preferably made of IVALON®, which can also be called a plug and corresponds to that of FIG. 5, so that reference to the description thereof can be made here.

Once the skeleton (166) has been surrounded by the IVALON® plug (168), the locking means (30), (32) and (34) are joined to the face ends (170), (172) of the closure body (168). The upper locking elements (30), (32), extending in a star pattern relative to one another, can be fixed by means of a double seam with three knots, while the single-ray locking means (34) can be fixed to the face end (172) by means of a triple seam with three knots. The corresponding connections are suggested purely in principle by reference numerals (174) (double seam with three knots) and (176) (triple seam with three knots).

It should also be mentioned that the preferred embodiment seen in FIGS. 11–14 need not necessarily have the middle part (148). Instead, the locking means (30, 32, 34) can be fixed to the closure body (168) solely by being firmly sutured.

Figure 15:
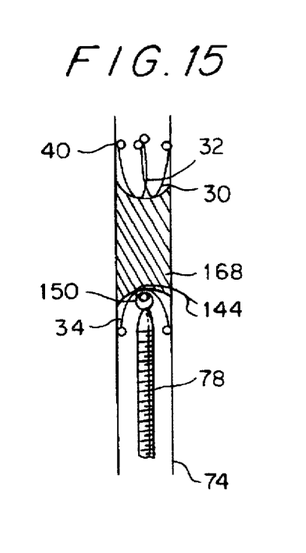
FIG. 15, the closure body of FIG. 13, positioned in a guide catheter.

An embodiment corresponding to the design of FIGS. 11–14 is shown in FIG. 15 in a position in which it has been inserted into a guide catheter (74). It can be seen that the plug (168) rests against the inner walls of the catheter (74), and that the locking elements (30), (32) and (34) rest with their ends (40) comprising titanium balls, on the inner wall of the guide catheter (74). The closure device is also grasped by means of a flexible pair of guide and fixing tongs (78) via the spherical formed-on feature (150). The closure device is also joined to the fixing tongs (78) via the safety thread (144).

Because of the frustoconical shape of the plug (168), the advantage is also attained that retraction of the closure device into the guide catheter (74), once the closure device has been extended out of it, can be done without the danger of injury, because in that case the lower locking elements (34) can first press against the frustoconical portion (178) of the plug (168), because there is an empty space between it and the guide catheter (74), since the diameter of the face end (172) is intended to be smaller than the inside diameter of the guide catheter (74).

FIGS. 16–20 show further features that should especially be emphasized of closure devices for closing a vascular opening.

Figure 16:
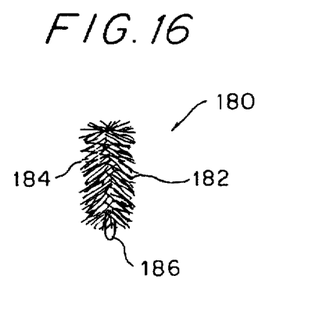
FIG. 16, a further embodiment to be emphasized of a closure device.
Figure 19:
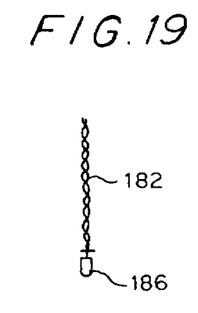
FIG. 19, a middle part suitable for a closure device of FIG. 16 or FIG. 17.
Figure 20:
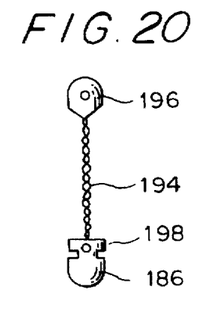
FIG. 20, a further middle part suitable for the closure device of FIG. 16 or FIG. 17.

A closure device (180) found in FIG. 16 comprises a middle part (182), which is coiled as shown in FIGS. 19 and 20, and from which intrinsically rigid but elastic threads, wires or bristles originate, in order to form a brushlike body (184) that forms a closure body. The protruding threads, wires or brushes should preferably be made of plastic.

The brush (184) has a cylindrical shape; for insertion of the closure device into a vascular opening, the threads, wires or bristles extend within the vascular opening to a circumference such as to injure the wall to promote clot formation. In addition, further fibers or other plastic elements can begin at the middle part (162), thus reinforcing clot formation.

The middle part (182) has a formed-on feature (186) on its end, so that—as described above—it can be engaged by tongs.

Figure 17:
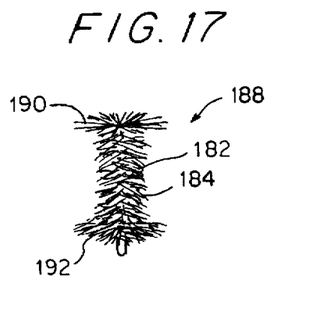
FIG. 17, a first further feature of the closure device of FIG. 16.

The exemplary embodiment found in FIG. 17 of a closure device (188) differs from that of FIG. 16 in that longer bristles or wires (190), (192), preferably of platinum, platinum alloy or titanium, extend above and below the cylindrical closure device (184); they perform the function of the locking means (30), (32), 34) of FIG. 11 and on their ends grow into vessel walls. Alternatively, and as shown in FIG.

Figure 18:
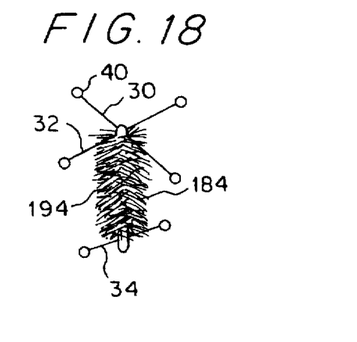
FIG. 18, a second further feature of the closure device of FIG. 16.

18, locking means (30), (32) and (34), corresponding for instance to FIG. 1 or FIG. 11, with spherical or lentiform ends (40) of titanium, for instance, may be provided. In addition, clot-promoting synthetic threads, fiberglass filaments or threads of natural materials such as cotton can originate at the middle part (182).

Middle parts of the closure devices (180), (188) are shown on a larger scale in FIGS. 19 and 20. It can be seen that the middle part (182) shown in FIG. 19 is coiled and has the formed-on feature (186) on its end. A middle part (194) that can be seen in FIG. 20 and is intended for a closure device of FIG. 18 is also coiled in the region of the closure body and has enlarged portions (196), (198) on its ends, which are penetrated by the locking means (30), (32), (34), as has been described in conjunction with FIG. 9. The formed-on feature (186) is then located below the enlarged portion (198).

Figure 21:
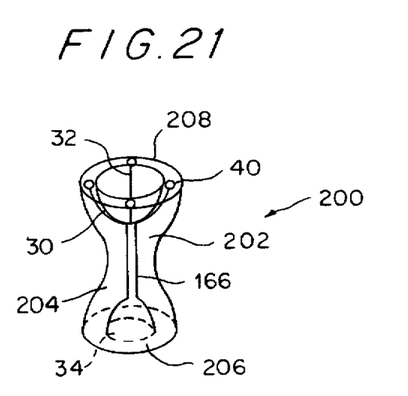
FIG. 21, a closure body with a skeleton surrounded by it.

In a further embodiment of a closure device (200), which can be found in FIG. 21, provision is made for the skeleton (166), found for example in FIG. 11, to be entirely surrounded by a closure body (202) made for example of IVALON®, so that this closure body comprises an indented middle portion (204) and widened outer portions (206) and (208). The latter portions (206), (208), along with the locking elements (30), (32), (34) extending in them and along with the end balls (40), which for instance are of polished titanium, extend outside the vascular opening that is to be closed. The tapered region (204) thus represents the actual closure body.

Although the closure body itself in the exemplary embodiments preferably has a cylindrical or frustoconical shape, other kinds of geometry are equally conceivable, because the form itself depends essentially on the defect, such as a vascular opening, that is to be closed. However, a frustoconical shape is considered to be preferable, for reasons given above.

Moreover it is not absolutely necessary for the locking or fixing elements to be embodied as rectilinear. Coiled or curved forms are equally conceivable. The locking means can also comprise textile or glass fibers or may have corresponding materials. Coating with plastic or metal is also possible.

The closure body itself may be of plastic, metal, ceramic or other suitable biocompatible materials.

It is also conceivable for the closure body in cross section to have a round, quadrilateral, hexagonal or octagonal geometry.

I claim:

1. A closure device (10, 42) for closing an anatomical anomaly in the form of a vascular opening (80), such as patent ductus arteriosus, atrial septal defect, foramen ovule or ventricular septal defect, said closure device including a closure body (14, 94, 168, 184) sized to extend at least within the vascular opening and said closure body being provided with a plurality of radially and freely projecting wirelike, resilient locking members (30, 32, 34) fixed to said closure body and adapted in use to extend outside the vascular opening, which resilient locking members comprising spherical or lentiform elements (40), and said resilient locking members (30, 32, 34) being fixed at radially inward ends to a middle part (18, 46, 148, 150, 182, 194), which extends in the axial direction of the closure body (40, 46, 94, 96, 168), which middle part in its axial length is generally within said closure body and has an integral coupling element (38, 58, 158, 186) in which use of the closure device (10, 42, 180, 188, 200) can be grasped by guide tongs (74) extending inside a catheter (72).

2. The closure device of claim 1, characterized in that the closure body (94, 96, 168) is embodied as rotationally symmetrical and at least in some regions as frustoconical.

3. The closure device of claim 1, characterized in that the closure body (94, 96, 168) has a cylindrical base portion (98, 100) and a frustoconical pointed portion (102, 104, 178), whose surface (106) follows a frustoconical jacket or a concave form, and preferably the base portion has a base surface with a diameter D1 which is at least 4 mm greater than a mean diameter MD measured over half the axial length of the closure body.

4. The closure device of claim 1, characterized in that the closure device is formed of a foamed material and the locking members (30, 32, 34) are fixed to the closure body by being foamed in place in the closure body.

5. The closure device of claim 1, characterized in that a securing element such as a safety thread (144) joined to the guide tongs (74) begins at at least one locking means (34) and/or the closure body (94, 168) and/or the middle part.

6. The closure device of claim 1, characterized in that the middle part (150) is embodied as adjustable in length and preferably comprises two portions (160, 162) that can be displaced in telescoping fashion relative to one another.

7. The closure device of claim 1, characterized in that the middle part (18, 46, 148, 150, 194), on its ends, has reinforcements (20, 22, 48, 50, 152, 158, 196, 198), to which the locking means (30, 32, 34) are fastened.

8. The closure device of claim 1, wherein said spherical elements (40) are polished laser welded beads or polished titanium balls.

9. The closure device of claim 1 characterized in that flexible elastic wires comprise, threads or bristles form the closure body (184) which threads or bristles begin at the middle part (182, 194) of the closure body.

10. The closure device of claim 9, characterized in that the threads of the closure body comprise soft fiber threads.

11. A closure device (10, 42) for closing an anatomical anomaly in the form of a vascular opening (80), such as patent ductus arteriosus, atrial septal defect, foramen ovale or ventricular septal defect, a closure body (14, 94, 168, 184) for extending at least within the vascular opening, and wirelike, elastic locking means (30, 32, 34) for extending outside the vascular opening, which locking means are provided with spherical or lentiform elements (40) on their free ends characterized in that:

the locking means (30, 32, 34) being positionally fixed with the closure body (94, 168) on the face end by suturing or extend entirely or nearly entirely within the closure body (202);

the locking means (30, 32, 34) being joined via a middle part (18, 46, 148, 150, 182, 194), which extends in the axial direction of the closure body (40, 46, 94, 96, 168) and in its axial length is generally within said closure body and has a formed-on feature (38, 58, 158, 186) that upon implantation of the closure device (10, 42, 180, 188, 200) can be grasped by guide tongs (74) extending inside a catheter (72); and wherein the middle part (150) being adjustable in length and comprising two portions (160, 162) that can be displaced in telescoping fashion relative to one another.

12. A closure device (10, 42) for closing an anatomical anomaly in the form of a vascular opening (80), such as patent ductus arteriosus, atrial septal defect, foramen ovale or ventricular septal defect, a closure body (14, 94, 168, 184) for extending at least within the vascular opening, and wirelike, elastic locking means (30, 32, 34) extending outside the vascular opening, which locking means are provided with spherical or lentiform elements (40) on their free ends characterized in that:

the locking means (30, 32, 34) being positionally fixed with the closure body (94, 168) on the face end by suturing or extend entirely or nearly entirely within the closure body (202);

the locking means (30, 32, 34) being joined via a middle part (18, 46, 148, 150, 182, 194), which extends in the axial direction of the closure body (40, 46, 94, 96, 168) and in its axial length has a formed-on feature (38, 58, 158, 186) that upon implantation of the closure device (10, 42, 180, 188, 200) can be grasped by guide tongs (74) extending inside a catheter (72); and wherein the middle part (18, 46, 148, 150, 194), on its end regions is provided with reinforcement means (20, 22, 48, 50, 152, 158, 196, 198) to which the locking means (30, 32, 34) are fastened.

* * * * *